United States Patent [19]

Smith et al.

[11] 4,160,818

[45] Jul. 10, 1979

[54] FLUORIMETRIC IMMUNOASSAY FOR DIPHENYLHYDANTOIN

[75] Inventors: David S. Smith; Adrienne R. McGregor, both of London, England

[73] Assignee: Technicon Instruments Corporation, Tarrytown, N.Y.

[21] Appl. No.: 787,232

[22] Filed: Apr. 12, 1977

[30] Foreign Application Priority Data

Apr. 15, 1976 [GB] United Kingdom ............... 15737/76
May 17, 1976 [GB] United Kingdom ............... 20323/76

[51] Int. Cl.² ...................... G01N 33/16; G01N 21/52
[52] U.S. Cl. ..................................... 424/8; 23/230 B; 424/12
[58] Field of Search ................. 23/230 B, 253 R, 259; 424/8, 12, 230 B

[56] References Cited

U.S. PATENT DOCUMENTS

| | | | |
|---|---|---|---|
| 2,797,149 | 6/1957 | Skeggs | 23/230 R |
| 3,901,654 | 8/1975 | Gross | 424/8 X |
| 3,995,021 | 11/1976 | Gross | 424/12 X |
| 3,996,345 | 12/1976 | Ullman | 23/230 B X |
| 3,998,943 | 12/1976 | Ullman | 424/12 |
| 4,036,946 | 7/1977 | Kleinerman | 424/12 X |

*Primary Examiner*—Sidney Marantz
*Attorney, Agent, or Firm*—S. P. Tedesco; Robert S. Salzman

[57] ABSTRACT

Substituted hydantoin drugs (for example phenytoin) and tricyclic antidepressant drugs (for example nortriptyline) are assayed by mixing them with a fluorescent labelled compound and antibodies, and measuring the fluorescence of the mixture. The assay does not necessitate any separation step and may be effected by continuous-flow techniques.

10 Claims, 5 Drawing Figures

FLUORIMETRIC IMMUNOASSAY FOR DIPHENYLHYDANTOIN

This invention is concerned with immunoassays and, more particularly, with a method of assaying diphenylhydantoin and nortriptyline, and similar drugs in biological fluid samples, such as blood serum for example.

Diphenylhydantoin (also known as 5,5-diphenylhydantoin, 5,5-diphenyl-2,4-imidazolidinedione, phenytoin, dilantin) is widely used as an anticonvulsant drug in the treatment and management of epilepsy. Its chemical formula is:

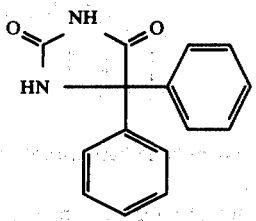

It is normally administered as the sodium salt, namely diphenylhydantoin sodium.

It is well established that the optimum therapeutic level of diphenylhydantoin (hereinafter "DPH") in blood (serum) is approximately 10 μg/ml. Lower levels will usually fail to control seizures, while at higher levels, undesirable side effects become evident. For example, nystagmus (involuntary rapid movement of the eyes) sets in at approximately 20 μg/ml, ataxia (failure of muscualr co-ordination) at approximately 30 μg/ml, and mental changes above about 40 μg/ml. Because of the narrow safe therapeutic range, it is general practice to monitor the blood levels of patients receiving DPH.

The most commonly applied assay for DPH at the present time is gas-liquid chromatography. Successive extraction steps followed by an evaporation step are necessary to isolate the drug from the serum sample before injection into a gas-liquid chromatograph and measurement of the peak corresponding to DPH on the resulting chromatogram. The extraction, evaporation and chromatography steps are all time-consuming and difficult to automate. Therefore, the sample throughput of this method is low. Comparatively large samples are required (typically 1 ml of serum) which can be a disadvantage, for example in pediatric practice.

In the past few years, several workers have raised antisera against DPH and developed immunoassays using these antisera. Radioimmunoassays using either $^{14}C$ or $^{3}H$ labelled DPH have been reported. These methods enable DPH concentrations in very small aounts (less than 1 μl) of serum to be measured. However, radiation hazards are involved, and expensive liquid scintillation counting equipment and reagents must be used. In addition, radioimmunoassays require a step in which the free and antibody-bound fractions of radio-labelled DPH are separated. It is desirable to avoid such steps if possible.

Immunoassays for DPH which involve neither radiolabelling nor a separation step have recently been described. In one version, drug molecules are covalently bound to an enzyme in such a way that the activity of the enzyme is inhibited when the attached drug molecules are bound by specific antiserum. DPH itself (for example from an added serum sample) will compete for the binding sites of the specific antiserum and reduce the extent of inhibition. A measurement of the enzyme activity can therefore be used as an estimate of the amount of added DPH. A two-point kinetic determination requiring one or two minutes is usually made using a suitably equipped spectrophotometer. Because of the kinetic end point, the assay as commonly used is not well suited to automation of the continuous-flow type.

A second type of non-separation immunoassay is based on "spin-labelling" of DPH with a free radical species. Such labelled DPH shows a different spectrum in an electron spin resonance (ESR) spectrometer depending on whether it freely rotates in solution, or is bound to specific anti-DPH antibody. In the presence of different amounts of DPH (for example from an added serum sample), the different free/bound ratios of the spin-labelled DPH can be monitored by recording an ESR spectrum, and the DPH concentration thereby estimated. This method requires complex and expensive equipment not found in the average clinical chemistry laboratory. Incubation times of 1 hour or more are required in such assay systems reported to date. Typically two to four minutes are required to scan an ESR spectrum. For the above reasons, such assays are not suited to automation of the continuous-flow type.

Nortriptyline is one of the most frequently used of the tricyclic antidepressant drugs, and is also important as a metabolite of amitriptyline.

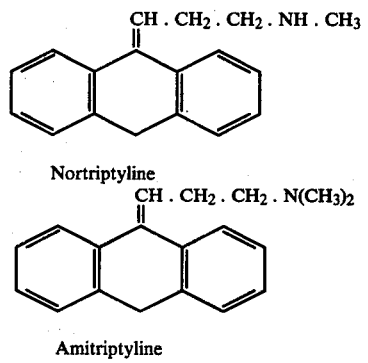

It is desirable to monitor the blood levels of these drugs because although there is a positive correlation between blood level and clinical improvement, considerable variations are found between the blood levels of individual patients receiving the same dose of drug.

At present, measurement is by spectrophotometric methods of barely adequate sensitivity, or by gas-liquid chromatography. These techniques involve time-consuming manipulations which are not susceptible to automation. Throughput is therefore low. Development of radioimmunoassays must await the availability of radio-labelled drugs of sufficient purity and activity.

We have now devised an immunoassay procedure for DPH, nortriptyline, and drugs of a similar chemical structure, which does not involve the use of radioactive materials and has a numbe of advantages over the assay procedures referred to above. In particular, we have found that these drugs can be sensitively assayed by a fluorscence quenching technique, which does not necessitate the use of very expensive apparatus or radiation hazards, and can be carried out on small samples relatively quickly. In addition, the procedure can be automated.

According to one aspect of the invention, there is provided a method of assaying a biological fluid sample for a drug selected from hydantoins and tricyclic antidepressant drugs, which comprises forming a mixture of the sample with a fluorescent-labelled compound (as herein defined) and antibody which is active against both the drug and the said compound, and measuring the fluorescence of the said compound in the mixture and thereby determining the amount of drug present in the sample.

The method of the invention is particularly useful for the assay of DPH, but it is also applicable to other similar drugs which contain the hydantoin ring or closely related structures, such as albutoin, aloxidone, 5-($\alpha,\beta$-dibromophenethyl)-5-methylhydantoin, 5,5-diphenyl-2-thiohydantoin, ethadione, ethosuximide, ethatoin, 5-ethyl-5-phenylhydantoin, mephenytoin, methetoin, methsuximide, 3-methyl-5-phenylhydantoin, paramethadione, pemoline, phensuximide, tetrantoin, and trimethadione, for example.

Amoung the tricyclic anti-derpessant drugs which can be assayed by the method of the invention are nortriptyline itself, and amitriptyline, butriptyline, desipramine, dibenzepin, hepzidine, imipramine, melitracene, opipramol, protriptyline and trimipramine.

By "fluorescent-labelled compound", we mean a compound which carries a fluorescent group, the fluorescence of which is reduced when the compound binds with the antibody in the method. Thus, the fluorescence of the mixture will be less than the fluorescence of the labelled compound alone, by an amount depending on the quantity of drug present in the original sample. By measuring the fluorescence of the mixture, and comparing it, for example, with a standard curve (described in more detail below), the amount of drug can be determined.

Thefluorescent-labelled compound has to be capable of complexing with the antibody used in the method, and the antibody must also be capable of complexing with the drug under analysis. It follows, therefore, that the labelled compound must either be of identical structure (apart from the label) to the drug under assay, or have a very closely similar structure since otherwise it will not bind with the antibody. Thus, the labelled compound to be used in the assay of a drug A will either be A itself carrying a fluorescent label, or a compound which is very similar to A (and which carries a fluorescent label). In the case of the nortriptyline-type drugs, some of which are very closely similar in structure, the labelled compound may be a different drug (with a label) from the drug under assay.

In the case of DPH itself, the preferred fluorescent label is fluorescein. It is not possible to react fluorescein (as the thiocyanate) directly with DPH, so we prefer to use, as the labelled compound, a compound which is sufficiently closely similar to DPH for it to be bindable with anti-DPH antibodies. (Alternatively, as is described below, the compound bearing the label must be sufficiently closely related to DPH for DPH to be bindable by antibodies produced against the compound to be labelled or other similar compound).

We have devised a fluorescein-labelled compound which is sufficiently close in structure to DPH for the purposes of this invention. It is fluoresceinthiocarbamyl-($\alpha,\alpha$-diphenylglycine) (hereinafter STC-DPG).

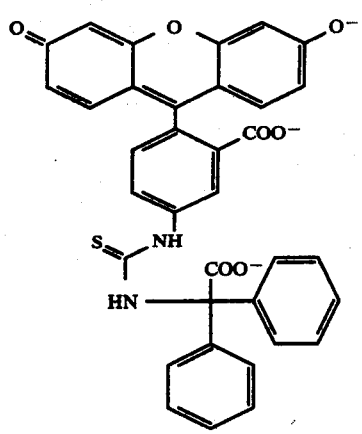

This compound is novel and forms another aspect of the present invention.

According to a further aspect of the invention, the compound is made by reacting the amino acid $\alpha,\alpha$-diphenylglycine with fluorescein isothiocyanate:

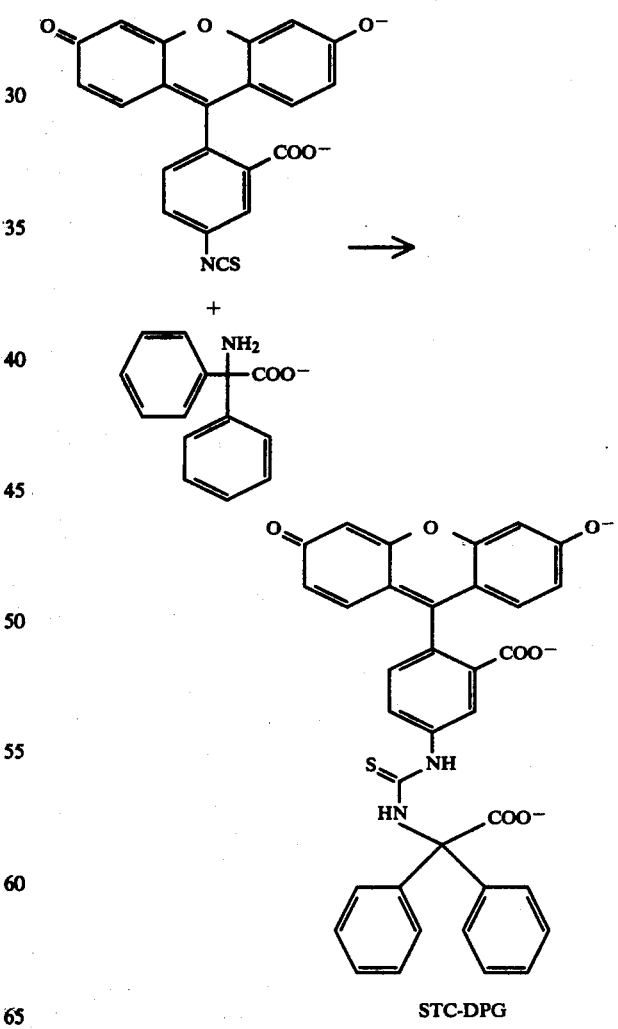

STC-DPG

It is in theory possible to cyclise STC-DPG to give 3-fluorescein-labelled 5,5-diphenyl-2-thiohydantoin:

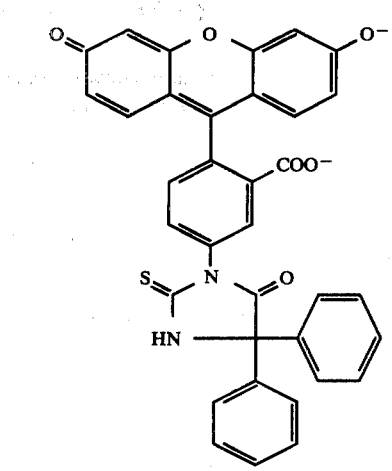

The invention further includes other hydantoin compounds similar to STC-DPG, which can be synthesised in a similar way and which themselves are sufficiently similar after fluorescent labelling to DPH and other related drugs for the purposes of this invention. The substituted compounds generally have little or no resemblance to the hydantoin being assayed prior to labelling. The labelling serving to both provide fluorescence and binding affinity with anti-compound antibodies. In particular, by the same general procedure described above, fluorescein-labelled compounds sufficiently similar, for the purposes of the present invention, to the following drugs can be made: albutoin, 5-($\alpha,\beta$-dibromophenethyl)-5-methylhydantoin, 5,5-diphenyl-2-thiohydantoin, ethotoin, 5-ethyl-5-phenylhydantoin, mephenytoin, methetoin, 3-methyl-5-phenyl-hydantoin and tetrantoin. The invention includes such fluorescein-labelled compounds and the process for their preparation.

In the assay of nortriptyline by the method of the invention, the preferred fluorescent label is fluorescein. This can be attached to nortriptyline by, for example, reacting nortriptyline with fluorescein isothiocyanate to give fluoresceinthiocarbamyl nortriptyline (hereafter "FTC-NT").

It is not essential in the method of the invention to use antibodies which have been raised using either the particular drug under assay or (where applicable) the closely related compound which is to carry the fluorescent label. The antibodies can, instead, be raised using another material but this will necessarily be closely similar in structure to the drug under assay and to the labelled compound, since otherwise the antiobdies will not bind with these two materials. As noted above, many drugs of the nortriptyline type have closely similar structures, so that antibody raised against one drug may be capable of complexing with another drug. Cross-reactivities of this type have the disadvantage of making assays of mixtures of two closely similar drugs, difficult to carry out. However, such an essay is very seldom required in practice. On the other hand, they have the advantage of enabling two or more drugs to be assayed using only one antiserum and/or only one fluorescent-labelled compound. This has significant advantages, both in reducing the stock of reactants required in an analytical laboratory, an of avoiding the necessity of labelling those drugs for which there can be difficult in attaching a fluorescent group.

In order to determine the amount of the drug under assay, from the fluorescence of the mixture formed in the method of the invention, it is convenient (but not essential) to use a standard curve.

A standard curve for any particular system (i.e. drug/fluorescent labelled compound/antibody) may, for example, be obtained as follows. Solutions of known concentration of the drug are made up in pooled normal serum or a suitable buffer. To each solution is added a constant known amount of fluorescent-labelled compound and sufficient specific anti-serum or immunoglobulin preparation to form a solution with a predetermined dilution. The fluorescence intensities of the solutions are then measured and a standard curve of fluorescence intensity against the concentration of unlabelled drug is plotted.

Such a curve may then be used in the method of the invention as follows: To a known volume of the biological fluid sample, which may comprise a buffer, is added the constant known amount of fluorescent-labelled compound used for preparing the standard curve. An amount of antiserum or immunoglobulin preparation is then added to provide the dilution thereof used in the standard curve determination. The fluorescence intensity of the resulting mixture is measured and from the standard curve, the amount of drug in the biological fluid sample can be determined.

Occasionally, a biological fluid sample to be assayed may contain serum proteins which might interfere with the assay of the invention, by, for example, non-specifically binding with the labelled compound. Where this situation arises or is suspected, the fluid sample should be treated, prior to the assay, to remove or inactivate the serum proteins, and methods for so doing are well known in the art.

In the method of the invention, it is preferred to mix the sample with the labelled compound, and then to combine the mixture with the antibody. Alternatively, the sample can be added to the antibody and the labelled compound added thereafter.

Whilst fluorescein is the preferred fluorescent label when assaying DPH or nortriptyline, other fluorescent groups can, in principle, be used including for example, dansyl, rhodamine, fluorescamine, pyrene and 2-methoxy-2,4-diphenyl-3(2$\underline{H}$)-furanone. The suitability of any particular fluorescent group with any particular drug/antibody system can readily be determined by routine trial and experiment. The fluorescent group should be one which is compatible with the system as a whole to show a reliable and reproducible fluorescent quenching effect upon formation of the labelled compound/antibody complex.

In this connection, it should be noted that the fluorescent quenching is dependent not only upon the particular fluorescent group used as label, but also upon the nature of the drug or other compound to which it is attached, the drug to be assayed and the antibody. The latter must also be selected having regard to its suitability in the overall system. Again, routine trial and experiment will reveal the suitability or otherwise of a particular antiserum or immunoglobulin preparation in a particular drug/fluorescent group system. We have found that with STC-DPG, an immunoglobulin preparation from a sheep antiserum produced by injecting DPH coupled to bovine serum albumin by the carbodiimide method is satisfactory. In the case of FTC-NT, sheep antisera produced by injecting N-(4-aminobutyl)nortriptyline coupled to bovine serum albumin by the carbodiimide method, are suitable.

It will be appreciated that the method of the invention includes the so-called "competitive binding" assay, in which there is competition between the labelled compound and the unlabelled drug (both antigens) to bind with a limited amount of antibody (antiserum or immunoglobulin preparation). Competitive binding immunoassays are very well known, and normally necessarily involve separation of the bound antibody:antigen complexes from free antigen. This separation step (which is, for example, necessary in radioimmunoassays) is a practical inconvenience. The method of the present invention, however, does not involve any separation step, and this makes the method ideally suited to analyses of the continuous-flow type. Accordingly, the invention includes the method herein described effected in a continuous-flow-manner, and also apparatus therefor.

In continuous flow analyses according to the present invention, the mixture of sample, antibody and fluorescent labelled compound, is passed along a conduit and the fluorescence is measured. In a preferred procedure, which is described in U.S. Pat. No. 2,797,149, individual segments of mixture are passed sequentially along the conduit, separated by an inert fluid segment (e.g. air) and, if desired, a wash liquid segment. The mixture can be formed in the conduit itself, by supplying to the conduit, in phase with segments of components of the mixture already present therein, the one or more further components, mixing of the components occurring in the conduit as the mixture flows therethrough.

It is a highly advantageous feature of the present invention that analyses of the drugs in question can be carried out relatively simply in this continuous flow manner, mainly as a result of the fact that no separation step is required in the method of the invention. Thus, the mixture flowing in the conduit may be passed directly to (or through) a fluorescence cell for direct measurement. It is therefore possible by the method of the invention to assay these particular drugs on a continuous flow basis which has been hitherto impossible or very difficult by prior known assay techniques.

Among the advantages of the present invention are the following:

1. STC-DPG and FTC-NT may be prepared from easily available and cheap starting products.
2. STC-DPG and FTC-NT have good shelf life.
3. Neither radiation hazard nor the need for radioactive counting facilities is involved.
4. No separation step is needed.
5. Measurement is by a single estimation made by conventional fluorimetry.
6. Because of points 4 and 5, the procedure can be automated easily.
7. The assay is fast. Only a few minutes are necessary for attainment of immunological equilibrium between antibody, STC-DPG and DPH, or antibody, FTC-NT and nortriptyline, for example.
8. The assay can be immunospecific for the particular drug (subject to cross-reactions referred to above).
9. The serum sample required is small. 1.5 λl or less suffices for a discrete assay of DPH, although somewhat larger quantities are required for nortriptyline.
10. Because of the small size of the serum sample, the contribution to the total signal of the intrinsic fluorescence of the serum sample itself can be negligible, although in any event it can easily be allowed for in the fluorescence measurements.

Figure 1:
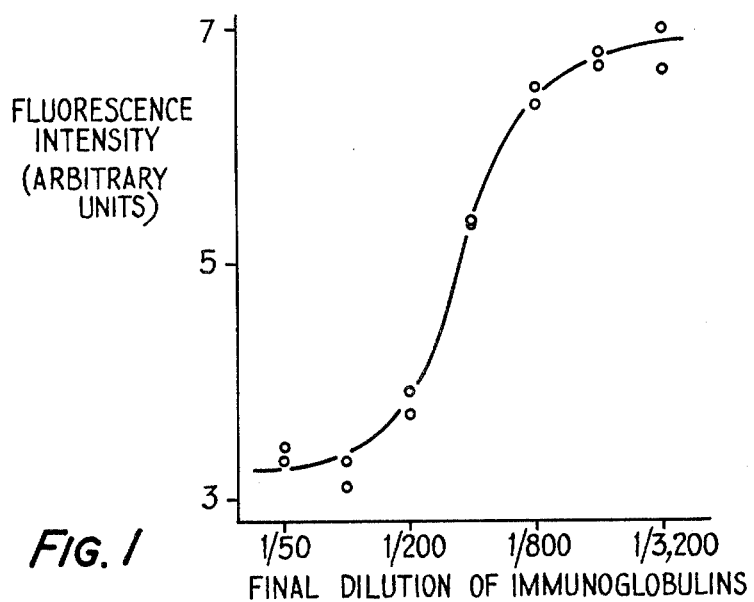
FIG. 1 shows a curve of fluorescence intensity vs. immunoglobulin dilutions to obtain optimum assay condition.

In order that the invention may be more fully understood, the following Examples are given by way of illustration only.

EXAMPLE 1. Preparation of STC-DPG

Solutions of α,α-diphenylglycine (43 mM) and fluorescein isothiocyanate (215 mM) were made up in pyridine/water/triethylamine 11:8:1 V/V. 1 ml of the α,α-diphenylglycine solution and 0.2 ml of the fluorescein isothiocyanate solution were mixed and left to stand for six days in the dark at room temperature. The products were precipitated by addition of 10 volumes of 0.2 M ammonium acetate, pH 4.0, and the precipitate centrifuged down and redissolved in one volume of 0.1 N NaOH. A 0.1 ml aliquot was subjected to preparative scale electrophoresis on a 5 cm wide strip of Whatman No. 17 paper in 0.02 M sodium carbonate/bicarbonate buffer, pH 9.0 for 2 h at approximately 10 volts/cm. Three fluorescent bands were separated, and after drying the strip, the middle band was cut out and the product eluted by shaking with 2 ml of 0.05 M ammonium bicarbonate.

The product was shown to be pure by the criteria of analytical electrophoresis on Whatman No. 1 paper in 0.02 M sodium carbonate/bicarbonate buffer, pH 9.0, and paper chromatography on Whatman No. 3MM paper using 0.05 M sodium carbonate/bicarbonate buffer, pH 9.0 as developer.

Assuming a peak extinction coefficient for the fluorescein group dianion of $8.72 \times 10^4$ 1 mole$^{-1}$ cm$^{-1}$ (quoted for fluorescein by Dandliker and Alonso, Immunochemistry 4, 191–196 (1967)), the concentration of the product solution was estimated to be 76 μM. Concentrations quoted below are based on this estimation.

The product was stored frozen and appears stable under these conditions.

EXAMPLE 2. Preparation of anti-DPH immunoglobulins

Anti-DPH serum from a sheep immunised with DPH coupled to bovine serum albumin by means of the carbodiimide method was the kind gift of Dr. G. W. Aherne, Dept. of Biochemistry, University of Surrey, Guildford, Surrey, England.

One volume of the antiserum was mixed with one volume of ammonium sulphate solution, 70% of saturated, pH 7.0, and left to stand for 4 h at room temperature. The precipitate was spun down and redissolved to the original serum volume by addition of deionised water. One volume of 70% ammonium sulphate was slowly added with mixing and the precipitate immediately spun down and redissolved to the original serum volume by addition of deionised water. The last step was repeated. The redissolved immunoglobulins were dialysed overnight against 0.1 M sodium phosphate buffer, pH 7.5, to give the desired product.

EXAMPLE 3. Destruction of STC-DPG binding proteins in human serum samples

Non-specific binding of STC-DPG to proteins (presumed to be mainly albumin) in human serum samples was obviated by enzymatic degradation in a pre-treatment step as follows. To 0.050 ml of human serum sample were added 1.95 ml of a 10 μg/ml solution of pepsin (from hog stomach mucosa, twice crystallised and lyophilised) in 0.1 N HCl. Incubation at 25° C. for 30 minutes was then shown to be sufficient to destroy all non-specific STC-DPG binding in the final fluorescence quenching immunoassay system (see below, Examples 4 and 5). At the pH of the assay system, pepsin is inactive and therefore does not interfere.

EXAMPLE 4. Flourescence quenching immunoassay for DPH (i) Antibody dilution curve.

In order to choose optimum assay conditions, a constant amount of STC-DPG in 0.1 M sodium phosphate pH 7.5 was added to doubling dilutions in the same buffer of the anti-DPH immunoglobulin preparation, so as to give a final STC-DPG concentration of 1 nM in a final volume of 1.5 ml. Fluorescence intensity was measured (see FIG. 1 of the accompanying drawings). From this curve a final immunoglobulin dilution of 1/200 was chosen for construction of the standard curve.

(ii) Standard curve.

To 0.050 ml samples of known concentration of DPH in pooled normal human serum was added 1.95 ml of pepsin solution (see Example 3). After incubation for 30 minutes at 25° C., 0.050 ml aliquots of the treated samples were added to 1 ml of 0.1 M sodium phosphate buffer pH 7.5, followed by the same amount of STC-DPG as used for construction of the antibody dilution curve. Then anti-DPH immunoglobulins were added to give a final dilution of 1/200 in a final volume of 1.5 ml. After a few minutes incubation at 25° C. to allow for equilibration, the fluorescence intensity of the assay mixtures was measured.

Figure 2:
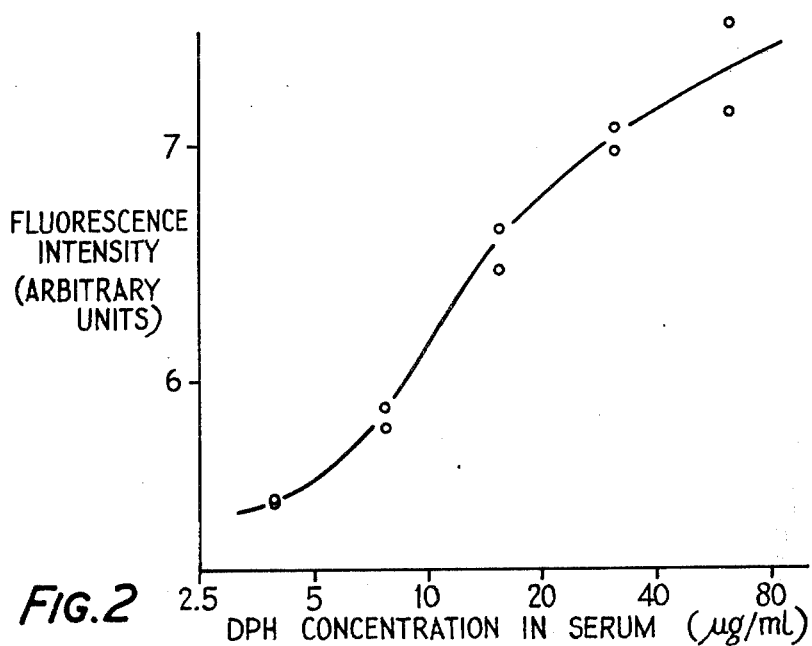
FIG. 2 shows a standard curve of fluroresence intensity vs. DPH concentration in serum.

The contribution of the intrinsic fluoresence of the pooled normal human serum to the total fluorescence intensity of the assay mixtures was measured by repeating the above procedure with phosphate buffer substituted for the STC-DPG and immunoglobulin solutions. By subtraction of the serum intrinsic fluorescence intensity from the total intensity of the assay mixtures, the standard curve shown in FIG. 2 was produced.

EXAMPLE 5. Assay of DPH in patient serum samples

Serum samples from patients receiving DPH therapy were assayed according to the procedure described in Example 4, section (ii). The contribution of the intrinsic fluorescence of each serum sample, measured independently, was subtracted from the total fluorescence intensity of the corresponding assay mixture, and the result used to determine, from an appropriate standard curve, the amount of drug in the serum assembly.

Figure 3:
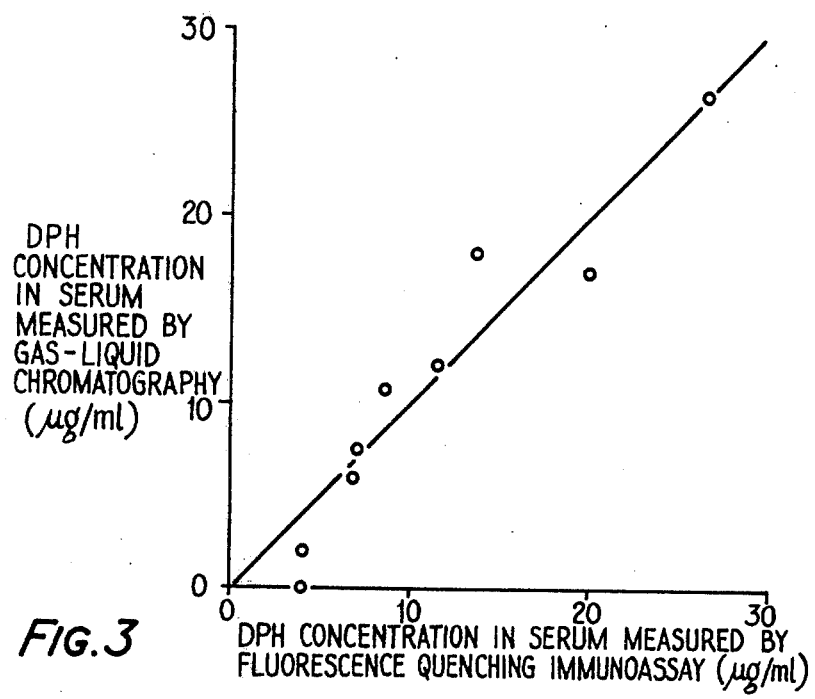
FIG. 3 shows a comparison of determining DPH concentration by GLC to the instant method.

FIG. 3 shows the correlation between DPH levels measured by fluorescence quenching immunoassay and levels measured by an independent laboratory using the established technique of gas-liquid chromatography. Agreement between the two methods is satisfactory for clinical purposes.

EXAMPLE 6. Continuous-flow system for automated assay of DPH

Figure 4:
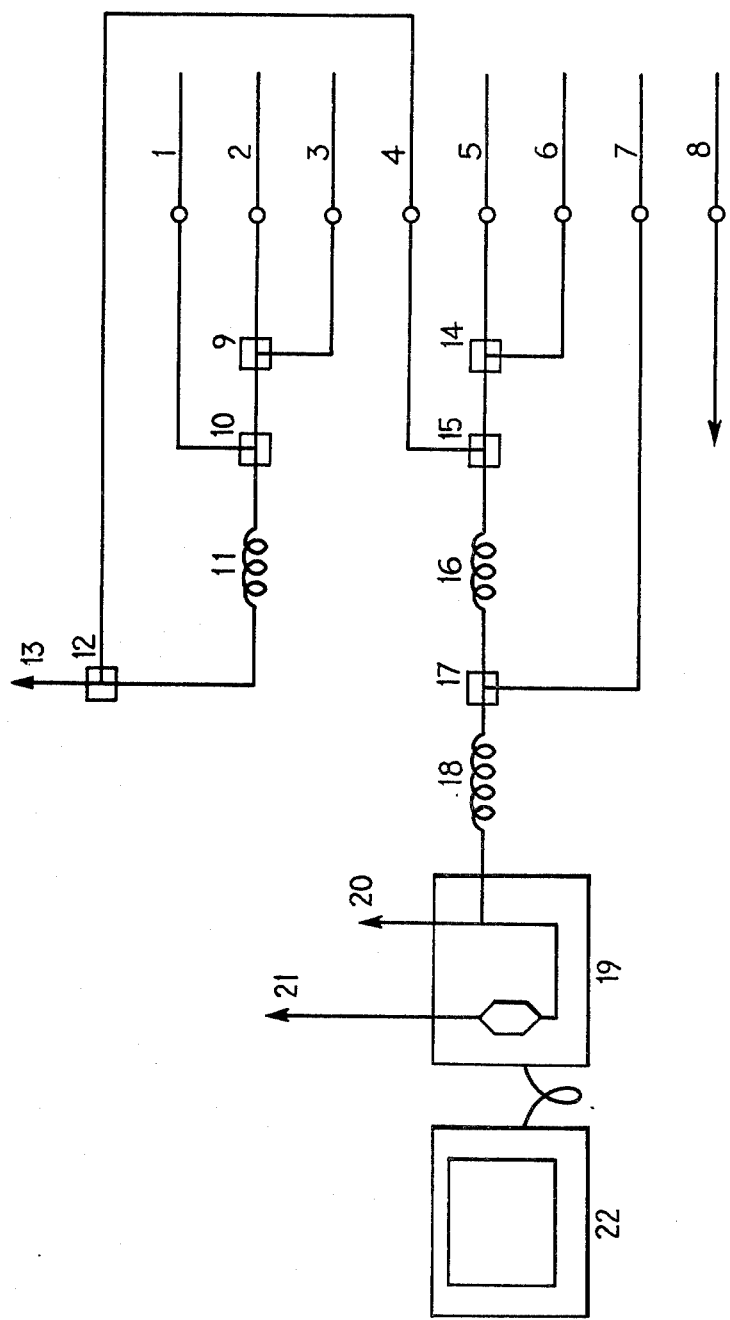
FIG. 4 is a diagram of one flow system for carrying out the instant immunoassay.

FIG. 4 of the accompanying drawings shows one form of flow system, suitable for a continuous-flow assay. The system comprises sample input line 1, pepsin reagent input line 2, air input line 3, pepsin-treated sample input line 4, STC-DPH input line 5, air input line 6, and antiserum or immunoglobulin input line 7. Lines 2 and 3 meet at segmenter 9 which is connected to junction 10 where line 1 joins line 2. Downstream of junction 10 line 2 is provided with mixing coil 11 and then passes to junction 12 where the stream is divided, one portion re-entering the system through line 4, the other passing to waste through outlet 13. Lines 5 and 6 meet at segmenter 14 which is connected to junction 15 where line 4 joins line 5. Downstream of junction 15 line 5 is provided with mixing coil 16 and then passes to junction 17 where line 7 joins. Downstream of junction 17 is mixing coil 18 and finally a fluorimeter 19 having a waste outlet 20 and an outlet 21 downstream of the fluorescence cell connected to line 8 and thence to waste. The fluorimeter 19 is operatively coupled to recorder 22.

In operation, a controlled amount of pepsin reagent (to destroy any interfering serum proteins) enters line 2 and is segmented by air in segmenter 9. The sample to be tested (e.g. serum) is introduced into the segmented stream in junction 10 followed by mixing and incubation in coil 11. A controlled amount of STC-DPG enters line 5 and is segmented by air in segmenter 14. A controlled amount of the pepsin-treated sample is re-sampled in junction 12 and introduced into the segmented STC-DPG stream in junction 15 followed by mixing in coil 16. Then a controlled amount of antiserum or immunoglobulins is introduced in junction 17 followed by mixing in coil 18 before passing to fluorimeter 19.

For measurement of the intrinsic fluorescence of samples (e.g. serum) in the continuous-flow system, aqueous buffer is substituted in lines 5 and 7.

EXAMPLE 7. Preparation of FTC-nortriptyline (FTC-NT)

6.7 mg/ml nortriptyline hydrochloride and 2.97 mg/ml fluorescein isothiocyanate (FITC) were made up in 0.05 M sodium carbonate/bicarbonate buffer, pH 9.0/MeOH 1:1 V/V. 0.3 ml of the FITC solution as mixed with 0.1 ml of the nortriptyline solution and left at room temperature for 105 minutes. The product was precipitated with 0.4 ml of 0.2 M ammonium acetate, pH 4.0, centrifuged down, and the supernatant discarded. After washing with 0.8 ml deionised water, the product was again spun down, and the supernatant discarded. The product was dissolved in 2 ml of 0.05 M ammonium bicarbonate with the help of added ammonia (0.01% final concentration by weight).

Paper chromatography (Whatman No. 3MM paper, developed with 0.05 M sodium carbonate/bicarbonate buffer, pH 9.0) and electrophoresis (Whatman No. 1 paper, 0.02 M sodium carbonate/bicarbonate buffer, pH 9.0 approx. 10 volts/cm) revealed only trace impurities in the product.

Assuming a peak extinction coefficient for the fluorescein group dianion of $8.72 \times 10^4$ 1 mole$^{-1}$ cm$^{-1}$ (quoted for fluorescein by Dandliker and Alonso, Immunochemistry 4, 191-196 (1967)), the concentration of the product solution was estimated to be 0.9 mM. Concentrations quoted below are based on this estimate.

The FTC-NT was stored in frozen solution and appears stable in this form.

EXAMPLE 8. Preparation of anti-nortriptyline immunoglobulins

Anti-nortriptyline serum raised in a sheep was the kind gift of Dr. G. w. Aherne, Dept. of Biochemistry, University of Surrey, Guildford, Surrey, England.

One volume of the antiserum was mixed with one volume of ammonium sulphate solution, 70% of saturated, pH 7.0, and left to stand for 4 h at room temperature. The precipitate was spun down and redissolved to the original serum volume by addition of deionised water. One volume of 70% ammonium sulphate was slowly added with mixing, and the precipitate immediately spun down and redissolved to the original serum volume by addition of deionised water. The last step was repeated. The redissolved immunoglobulins were dialysed overnight against 0.1 M sodium phosphate buffer, pH 7.5, to give the desired product.

Figure 5:
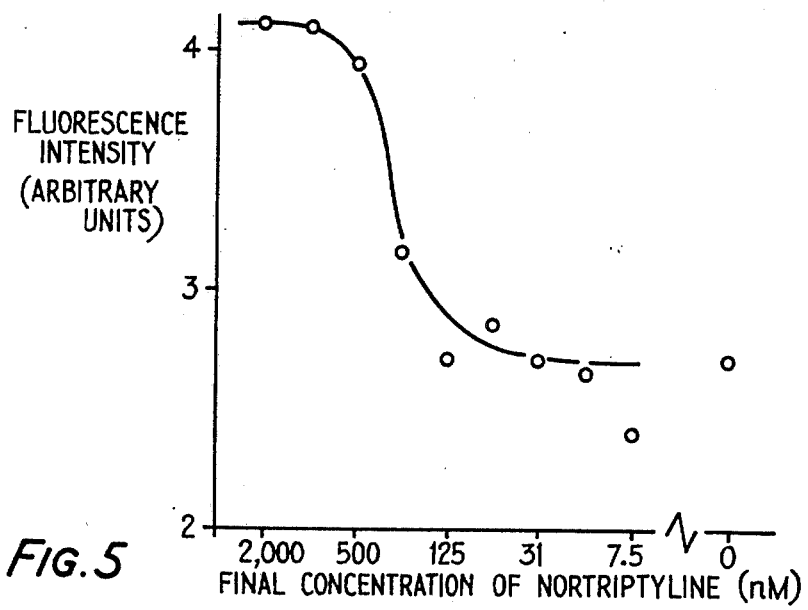
FIG. 5 shows a standard curve of fluorescence intensity vs. concentration of nortriptyline.

EXAMPLE 9. Flourescence quenching immunoassay for nortriptyline: standard curve To 0.1 ml samples of nortriptyline of known concentration in 0.075 M barbital buffer, pH 8.8, was added 1.4 ml of the preparation of anti-nortriptyline immunoglobulins diluted 1/28 in the same buffer. After a few minutes at 25° C., 0.05 ml of a 750 mM solution of FTC-NT in the same buffer was added. After 45 minutes at 25° C., the fluoresence of the mixtures was measured (see FIG. 5). The final concentration of FTC-NT was 24nM and the final dilution of anti-nortriptyline immunoglobulines was 1/31.

We claim:

1. A method of assaying a biological fluid sample for a hydantoin or a closely related hydantoin structured compound, said method comprising the steps of:
   a. forming a mixture of said biological fluid sample containing said compound to-be-assayed with: (1) anti-compound antibodies, and (2) a fluorescent-labelled substituted compound, said substituted compound generally having little or no resemblance to said compound to-be-assayed prior to labelling but, having sufficient similarity to said compound to-be-assayed after labelling, so as to be bindable with said anti-compound antibodies, said anti-compound antibodies binding both with said compound to-be-assayed and said fluorescent-labelled substituted compound; and
   b. determining the amount of said compound in the fluid sample by measuring the fluorescence of said fluorescent-labelled substituted compound.

2. The method according to claim 1, wherein the compound under assay is further selected from a group consisting of: diphenylhydantoin, albutoin, aloxidone, 5-($\alpha,\beta$-dibromophenethyl)-5-methylhydantoin, 5,5-diphenyl-2-thiohydantoin, ethadione, ethosuximide, ethatoin, 5-ethyl-5-phenylhydantoin, mephenytoin, methetoin, methsuximide, 3-methyl-5-phenyl-hydantoin, paramethadione, pemoline, phensuximide, tetrantoin, and trimethadione.

3. The method according to claim 1, wherein the fluorescent-labelled substituted compound is labelled with a fluorescent label which is selected from a group consisting of: fluorescein, dansyl, rhodamine, fluorescamine, pyrene and 2-methoxy-2,4-diphenyl-3(2H)-furanone.

4. The method according to claim 1, wherein the measurement of the fluorescence of the mixture is compared with the fluorescence of standard mixtures containing known amounts of the compound under assay, and the amount of compound in the sample is thereby determined.

5. The method of claim 1, further comprising the step of:
   c. adding pepsin to said biological sample prior to forming said mixture.

6. The method of assaying a biological fluid sample of claim 1, further comprising the step of:
   c. flowing said mixture past a fluorimeter to measure the fluorescence of said mixture.

7. The method of claim 1, wherein the compound to-be-assayed is diphenylhydantoin, and said fluorescent-labelled substituted compound is fluorescein thiocarbamyl-($\alpha,\alpha$-diphenylglycine).

8. The method of claim 1, wherein said anti-compound antibodies were raised against said fluorescent-labelled substituted compound.

9. A method according to claim 1, wherein the fluorescent-labelled substituted compound is fluoresceinthiocarbamyl-($\alpha,\alpha$-diphenylglycine).

10. A method according to claim 9, wherein the fluorescein thiocarbamyl-($\alpha,\alpha$-diphenylglycine) has been obtained by reacting $\alpha,\alpha$-diphenylglycine with fluorescein isothiocyanate.

* * * * *